(12) United States Patent
Ueda et al.

(10) Patent No.: US 10,786,375 B2
(45) Date of Patent: Sep. 29, 2020

(54) STENT

(71) Applicant: TERUMO KABUSHIKI KAISHA, Tokyo (JP)

(72) Inventors: Ryosuke Ueda, Fuji (JP); Tomoya Komatsu, Hadano (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 142 days.

(21) Appl. No.: 16/118,753

(22) Filed: Aug. 31, 2018

(65) Prior Publication Data

US 2018/0369000 A1 Dec. 27, 2018

Related U.S. Application Data

(63) Continuation of application No. PCT/JP2017/001781, filed on Jan. 19, 2017.

(30) Foreign Application Priority Data

Mar. 16, 2016 (JP) .................................. 2016-053085

(51) Int. Cl.
*A61F 2/90* (2013.01)
*A61F 2/915* (2013.01)
(Continued)

(52) U.S. Cl.
CPC .................. *A61F 2/90* (2013.01); *A61F 2/91* (2013.01); *A61F 2/915* (2013.01); *A61F 2/958* (2013.01);
(Continued)

(58) Field of Classification Search
CPC ...... A61F 2/04; A61F 2/06; A61F 2/82; A61F 2/86; A61F 2/89; A61F 2/90;
(Continued)

(56) References Cited

U.S. PATENT DOCUMENTS

| 5,718,713 A | 2/1998 | Frantzen |
| 6,309,414 B1 * | 10/2001 | Rolando .................. A61F 2/91 623/1.15 |

(Continued)

FOREIGN PATENT DOCUMENTS

| CN | 102448406 A | 5/2012 |
| EP | 3 431 049 A1 | 1/2019 |

(Continued)

OTHER PUBLICATIONS

International Search Report (PCT/ISA/210) dated May 16, 2017, by the Japanese Patent Office as the International Searching Authority for International Application No. PCT/JP2017/001781.
(Continued)

*Primary Examiner* — Ashley L Fishback
(74) *Attorney, Agent, or Firm* — Buchanan Ingersoll & Rooney PC

(57) ABSTRACT

A stent including linear struts forming an outer periphery of a cylindrical shape in which a gap is formed, a link portion connecting the struts to each other in the gap, and a connection extension portion extending along a connection direction of the link portion. The link portion includes a first curved portion provided on one end in the connection direction, and curves to protrude inward in the radial direction, and a second curved portion provided on the other end of the connection direction, and curves to protrude inward in the radial direction. The connection extension portion includes a first gradually decreasing portion gradually decreasing from the first curved portion toward an edge on one end of the connection direction, and a second gradually decreasing portion gradually decreasing from the second curved portion toward an edge on the other end of the connection direction.

18 Claims, 6 Drawing Sheets

(51) Int. Cl.
   *A61F 2/91* (2013.01)
   *A61F 2/06* (2013.01)
   *A61F 2/958* (2013.01)

(52) U.S. Cl.
   CPC ............ *A61F 2002/068* (2013.01); *A61F 2002/91558* (2013.01); *A61F 2210/0004* (2013.01); *A61F 2220/0025* (2013.01); *A61F 2230/0019* (2013.01); *A61F 2230/0069* (2013.01); *A61F 2240/001* (2013.01); *A61F 2250/0036* (2013.01); *A61F 2250/0067* (2013.01)

(58) Field of Classification Search
   CPC .... A61F 2002/9155; A61F 2002/91558; A61F 2002/91566; A61F 2002/91575; A61F 2002/91583
   See application file for complete search history.

(56) References Cited

U.S. PATENT DOCUMENTS

| | | |
   |---|---|---|
   | 6,736,844 B1 | 5/2004 | Glatt et al. |
   | 2006/0136041 A1 | 6/2006 | Schmid et al. |
   | 2012/0165923 A1 | 6/2012 | Maruyama et al. |
   | 2012/0214384 A1 | 8/2012 | Harder |
   | 2012/0285836 A1 | 11/2012 | von Oepen |
   | 2015/0223954 A1 | 8/2015 | Jang et al. |

FOREIGN PATENT DOCUMENTS

| | | |
|---|---|---|
| JP | 2002501409 A | 1/2002 |
| JP | 2008523914 A | 7/2008 |
| JP | 2014226353 A | 12/2014 |
| WO | 2008150719 A1 | 12/2008 |
| WO | 2009/070624 A1 | 6/2009 |

OTHER PUBLICATIONS

Written Opinion (PCT/ISA/237) dated May 16, 2017, by the Japanese Patent Office as the International Searching Authority for International Application No. PCT/JP2017/001781.

The extended European Search Report dated Sep. 13, 2019, by the European Patent Office in corresponding European Patent Application No. 17766041.2-1113. (8 pages).

An English Translation of the International Search Report (Form PCT/ISA/210) and the Written Opinion of the International Searching Authority (Form PCT/ISA/237) dated May 16, 2017, by the Japanese Patent Office in corresponding International Application No. PCT/JP2017/001781. (9 pages).

Office Action (The First Office Action) dated Mar. 2, 2020, by the State Intellectual Property Office of People's Republic of China in corresponding Chinese Patent Application No. 201780017749.9, and an English Translation of the Office Action. (16 pages).

* cited by examiner

STENT

CROSS-REFERENCE TO RELATED APPLICATIONS

This application is a continuation of International Application No. PCT/JP2017/001781, filed on Jan. 19, 2017, which claims priority to Japanese Application Number 2016-053085, filed on Mar. 16, 2016, the entire content of both being incorporated herein by reference.

TECHNICAL FIELD

The present invention relates to a stent.

BACKGROUND DISCUSSION

A stent, for example, is indwelled in an expanded state in a stenosed site or an occlusion site formed in a blood vessel and maintains an open state of the blood vessel.

Such a stent, in which linear struts (cylindrical body) are connected to each other by a link portion (connection section) is shown for example in Japanese Application No. JP-A-2014-226353.

In a case where the stent disclosed in JP-A-2014-226353 is indwelled in the blood vessel, there is a concern that blood flow is disturbed by the stent, and blood does not flow well. A phenomenon in which the blood flow is disturbed occurs particularly in a vicinity of a link portion connecting the struts to each other. This is due to a relatively complex structure in the vicinity of the link portion. As described above, in a case where the blood does not flow well in the vicinity of the link portion, there is a possibility that a thrombus is formed in the vicinity of the link portion.

The disclosure herein provides a stent capable of suppressing formation of a thrombus in a vicinity of a link portion.

SUMMARY

According to the disclosure herein, there is provided a stent including linear struts that form an outer periphery of a cylindrical shape in which a gap is formed, a link portion that connects the struts to each other in the gap, and a connection extension portion that extends along a connection direction of the link portion. The link portion includes, in a cross section along the connection direction, a first curved portion that is provided on one end of the connection direction and curves to protrude inward in a radial direction, and a second curved portion that is provided on the other end of the connection direction and curves to protrude inward in the radial direction. The connection extension portion includes, in a cross section along the connection direction, a first gradually decreasing portion that is linked while gradually decreasing from the first curved portion toward an edge on one end of the connection direction, and a second gradually decreasing portion that is linked while gradually decreasing from the second curved portion toward an edge on the other end of the connection direction.

According to the above-described stent, a stream or stream-lined shape is provided inward in the radial direction of the stent using a link portion and a connection extension portion, and the blood flows along the link portion and the connection extension portion. Accordingly, since the blood flows along the stream shape provided in a range longer than the connection direction, the blood flows well along the connection direction. Therefore, it is possible to suppress formation of a thrombus in the vicinity of the link portion.

DESCRIPTION OF EMBODIMENTS

Figure 1:
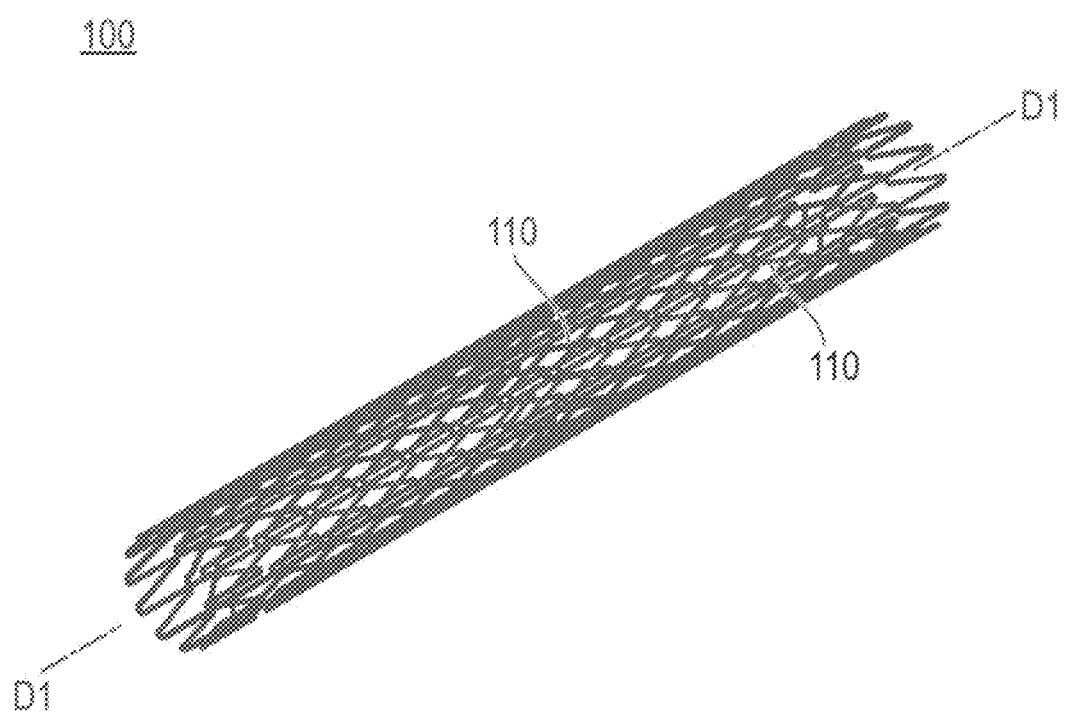
FIG. 1 is a perspective view of a stent according to an exemplary embodiment of the disclosure.

Hereinafter, an exemplary embodiment of the disclosure will be described with reference to the accompanying drawings. Note that, dimensional ratios in the drawings are exaggerated and are different from the actual ratios for the convenience of description.

FIGS. 1 to 5 are schematic views showing a structure of a stent 100 according to an exemplary embodiment of the disclosure herein. Hereinafter, the stent 100 of the embodiment will be described with reference to FIGS. 1 to 5.

Figure 2:
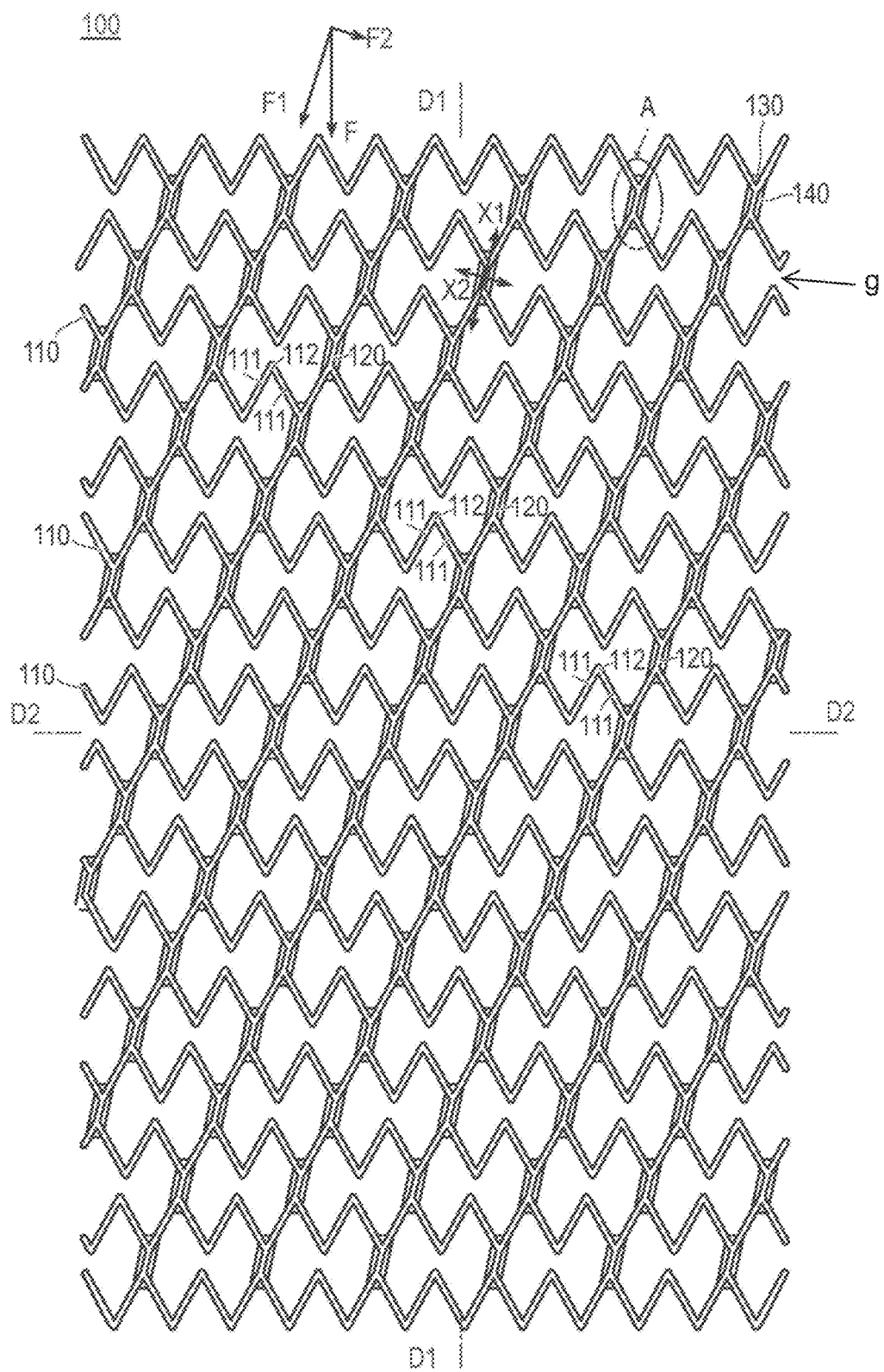
FIG. 2 is a plan view in which a part of an outer periphery of the stent of the exemplary embodiment has been linearly cut along an axial direction.

As shown in FIGS. 1 and 2, the stent 100 of the exemplary embodiment includes struts 110, which are linear components, and a link portion 120 connecting the struts 110 to each other, a connection extension portion 130 that extends along a connection direction X1 of the link portion 120, and an orthogonal extension portion 140 that extends along an orthogonal direction X2 that is orthogonal to the connection direction X1 of the link portion 120.

Figure 3:
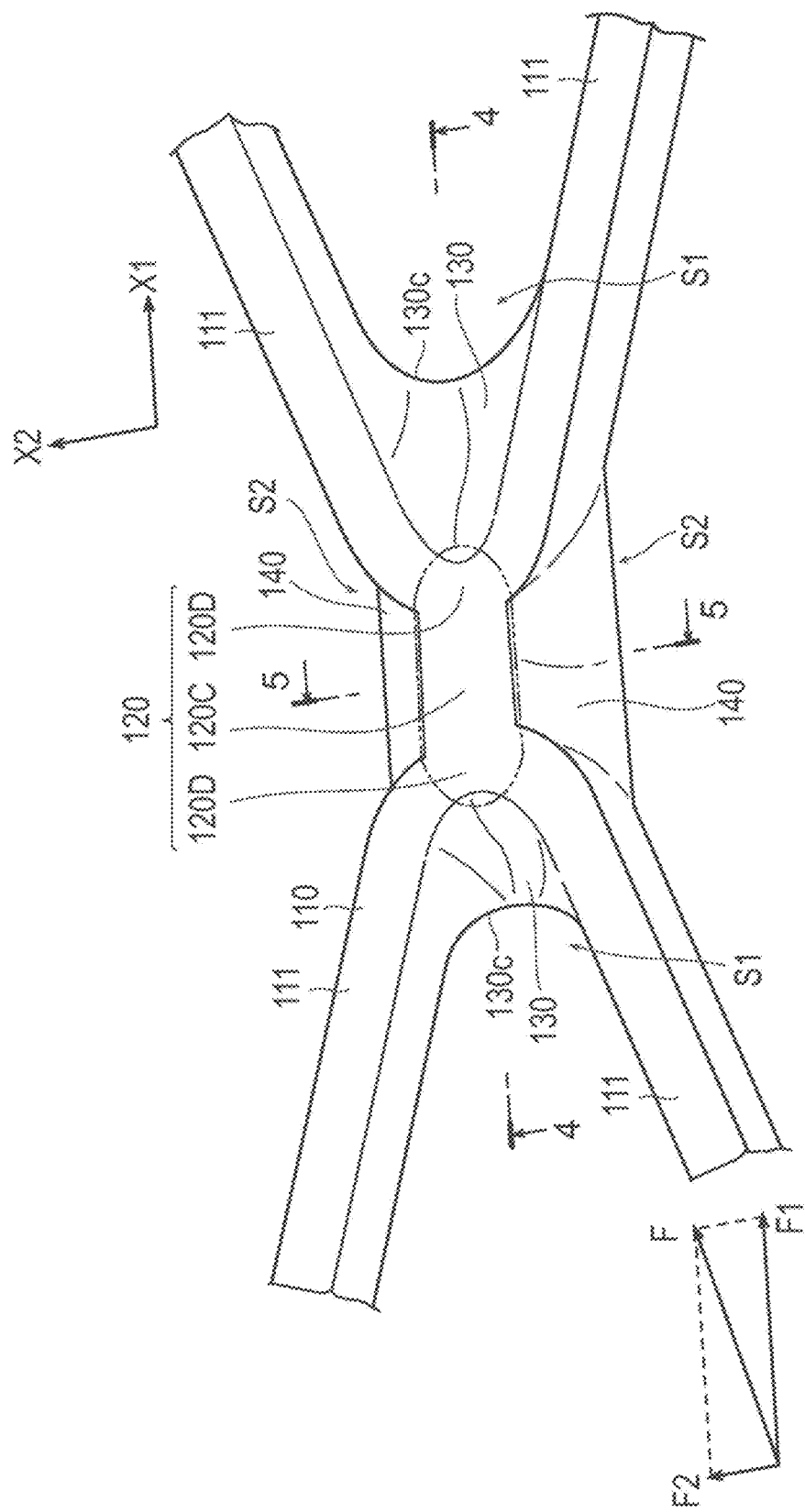
FIG. 3 is a schematic perspective view of a portion A of FIG. 2.
Figure 4:
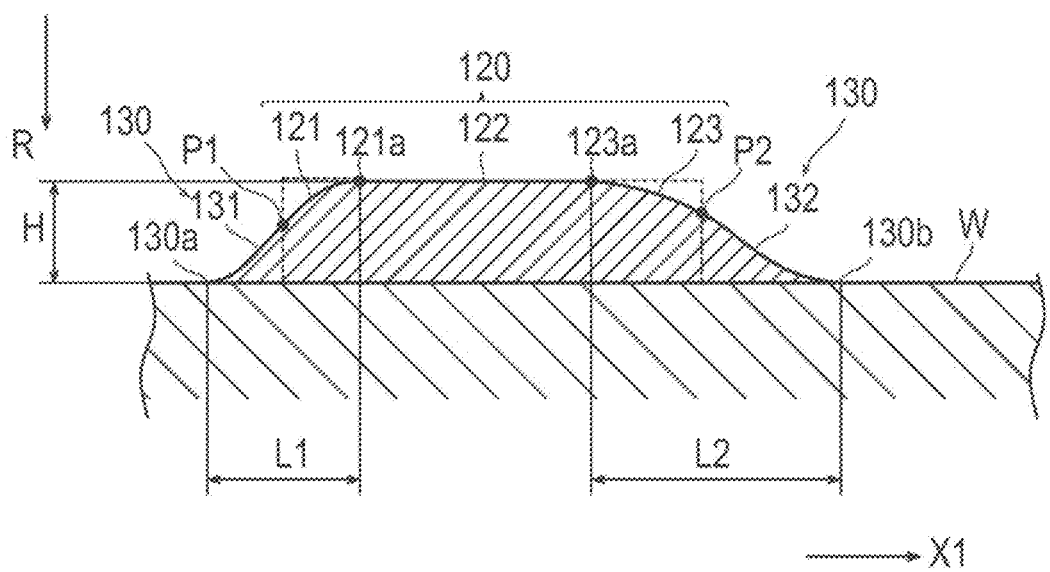
FIG. 4 is a cross-sectional view taken along line 4-4 of FIG. 3.
Figure 5:
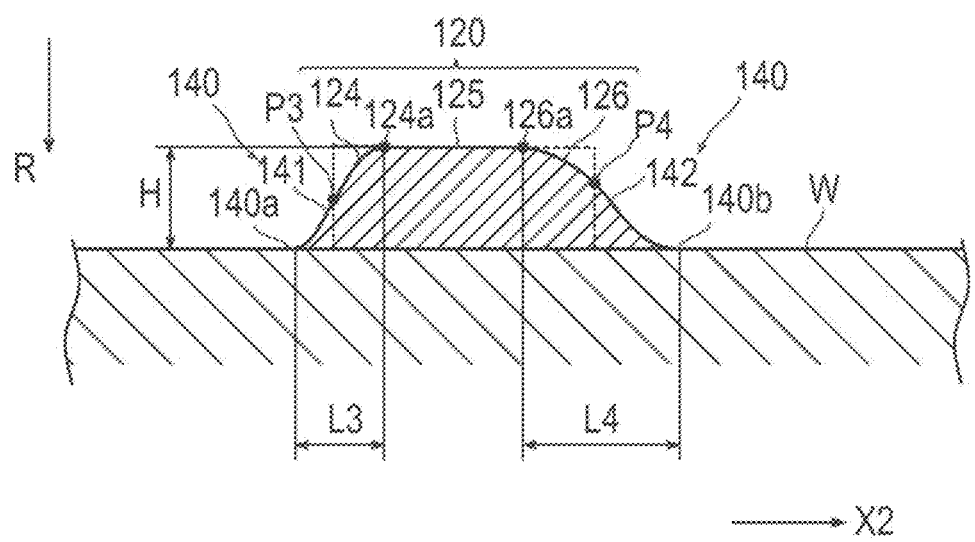
FIG. 5 is a cross-sectional view taken along line 5-5 of FIG. 3.

Note that, in the disclosure here, an axial direction of a cylindrical shape formed using the struts 110 is simply denoted as an "axial direction D1" (refer to FIGS. 1 and 2), a circumferential direction of the cylindrical shape is simply denoted as a "circumferential direction D2" (refer to FIG. 2), a radial direction of the cylindrical shape is simply denoted as a "radial direction R" (refer to FIGS. 4 and 5). In addition, a side inserted into the blood vessel is denoted as a "distal side", and a hand operation side that is opposite to the distal side is denoted as a "proximal side". Moreover, a direction that the link portion 120 connects the struts 110 to each other is denoted as the "connection direction X1", and a direction that is orthogonal to the connection direction X1 is denoted as the "orthogonal direction X2" (see FIG. 2). In addition, in blood flow F along the axial direction D1, blood flow along the connection direction X1 is denoted as "blood flow F1", and blood flow along the orthogonal direction X2 is denoted as "blood flow F2" (see FIGS. 2 and 3).

The struts 110 form an outer periphery of the cylindrical shape in which a gap g is formed between adjacent struts, as shown best in FIG. 2. As shown in FIG. 2, the struts 110 have a plurality of main strut portions 111 and a plurality of bent portions 112 that interlock the main strut portions 111 that extend in directions different from each other. The struts 110 extend in the circumferential direction D2 while being folded back in a wave shape to form an endless tubular shape.

The plurality of the struts 110 are provided along the axial direction D1 as shown in FIG. 2. The plurality of struts 110 provided along the axial direction D1 is connected to each other through the link portion 120.

The main strut portions 111 have, for example, a rectangular cross section along a width direction. According to this configuration, since it is possible to increase volume of the main strut portions 111 compared with a case where the cross section of the main strut portion is formed in a stream shape, to be described later, when the stent 100 expands, it is possible to impart a desired expansion force with respect to a blood vessel wall W. Accordingly, it is possible to suitably maintain the open state of the blood vessel.

The link portion 120 connects the struts 110 to each other in the gap g between adjacent struts 110 (between bent portions 112) along the axial direction D1 as shown in FIG. 2. In the exemplary embodiment, the link portion 120 refers to, as is indicated with two-dot chain line in FIG. 3, a portion where an interlock portion 120C interlocks the struts 110 to each other and both end portions 120D provided on both sides in the connection direction X1 are combined with the interlock portion 120C interposed in between. In other words, the link portion 120 refers to, in the cross-sectional shape along the connection direction X1 described later, a portion provided in a range excluding the connection extension portions 130 (see FIG. 4).

As shown in FIG. 2, the link portion 120 according to the exemplary embodiment is provided along the connection direction X1 inclined by a predetermined angle from the axial direction D1. Note that, the link portion 120 may be provided along the axial direction D1.

The plurality of link portions 120 is disposed at predetermined intervals in the circumferential direction D2. Note that, a location where the link portion 120 is disposed is not limited to a location shown in FIG. 2 and can be appropriately changed as long as the plurality of struts 110 provided along the axial direction D1 are connected to each other.

As shown in FIG. 3, the connection extension portion 130 is configured to extend along the connection direction X1 so as to fill in a gap S1 formed between the main strut portions 111 that extend in directions different from each other in the connection direction X1. The connection extension portion 130 is provided on an upstream side and a downstream side of the blood flow F1 along the connection direction X1, respectively.

As shown in FIGS. 2 and 3, the connection extension portion 130 has a concave portion 130c that is arcuately recessed toward the link portion 120. The concave portion 130c is provided on the upstream side and the downstream side of the blood flow F1 along the connection direction X1, respectively. The connection extension portion 130 is formed in a paddle or arcuate shape.

As shown in FIG. 4, the connection extension portion 130 protrudes inward in the radial direction R together with the link portion 120.

As shown in FIGS. 2 and 3, the orthogonal extension portion 140 is configured to extend along the orthogonal direction X2 so as to fill in a gap S2 formed between adjacent main strut portions 111 in the axial direction D1 in the orthogonal direction X2. The orthogonal extension portion 140 is provided on an upstream side and a downstream side of the blood flow F2 along the orthogonal direction X2, respectively.

As shown in FIG. 5, the orthogonal extension portion 140 protrudes inward in the radial direction R together with the link portion 120.

The stent 100 is integrally formed with the struts 110, the link portion 120, the connection extension portion 130, and the orthogonal extension portion 140.

The material forming the stent 100 is, for example, a biodegradable material which is degraded in vivo. Examples of such a material include biodegradable synthetic polymeric materials such as polylactic acid, polyglycolic acid, lactic acid-glycolic acid copolymers, polycaprolactone, lactic acid-caprolactone copolymers, glycolic acid-caprolactone copolymers, and poly-γ-glutamic acid, biodegradable natural polymer materials such as collagen, biodegradable metallic materials such as magnesium and zinc.

The manufacturing method of the stent 100 is not particularly limited, but, examples thereof include a method of cutting out from a tube made of the above-described materials with laser or the like, a method by an injection molding, a method (laminate molding) of laminating using a 3D printer or the like. From a viewpoint of precisely finishing a complicated cross-sectional shape, a method by an injection molding or a method of laminating using a 3D printer are preferable. Furthermore, from a viewpoint of manufacturing at a low cost and a viewpoint of finishing as a smooth surface condition, a method by an injection molding is particularly preferable.

In addition, the stent 100 may include a coating body (not shown) containing a medicine on its surface. The coating body is formed on an outer surface side of the stent 100 which is to be come into contact with a blood vessel wall, but the disclosure herein is not limited thereto.

The coating body contains a medicine capable of suppressing proliferation of neointima, and a medicine carrier for carrying the medicine. Note that the coating body may be formed of only the medicine. The medicine contained in the coating body is at least one selected from the group consisting, for example, of sirolimus, everolimus, zotarolimus, and paclitaxel. The constituent material of the medicine carrier is not particularly limited, but a biodegradable material is preferable, and the same material as that of the stent 100 is applicable.

Next, a cross-sectional shape along the connection direction X1 of the link portion 120 and the connection extension portion 130 will be described with reference to FIG. 4. Note that, in FIG. 4, a state where the link portion 120 and the connection extension portion 130 are compressed to the blood vessel wall W is shown. In addition, in FIG. 4, an upper side of the drawing is a blood flow side, and a lower side thereof is the blood vessel wall W side. The blood flow F1 along the connection direction X1 in the blood flow F flows along the stream shape of the cross section along the connection direction X1 of the link portion 120 and the connection extension portion 130.

As shown in FIG. 4, the link portion 120 has, in a cross section along the connection direction X1, a first curved portion 121, a linear portion 122, and a second curved portion 123 provided in order from the upstream side (left side of FIG. 4) of the blood flow F1.

The first curved portion 121 curves to protrude inward (upper side of FIG. 4) in the radial direction R.

The linear portion 122 is provided smoothly and continuous to the first curved portion 121 in an end portion 121a on a downstream side of the first curved portion 121. In the disclosure herein, "smoothly" means a state without stages and edges.

The second curved portion 123 curves to protrude inward (upper side of FIG. 4) in the radial direction R. In addition, the second curved portion 123 is configured such that a tangent line in an end portion 123*a* on an upstream side of the second curved portion 123 extends along the linear portion 122. The second curved portion 123 is configured to have a curvature smaller than the first curved portion 121.

The second curved portion 123 is provided smoothly and continuous to the linear portion 122 in the end portion 123*a* on the upstream side of the second curved portion 123.

Figure 6:
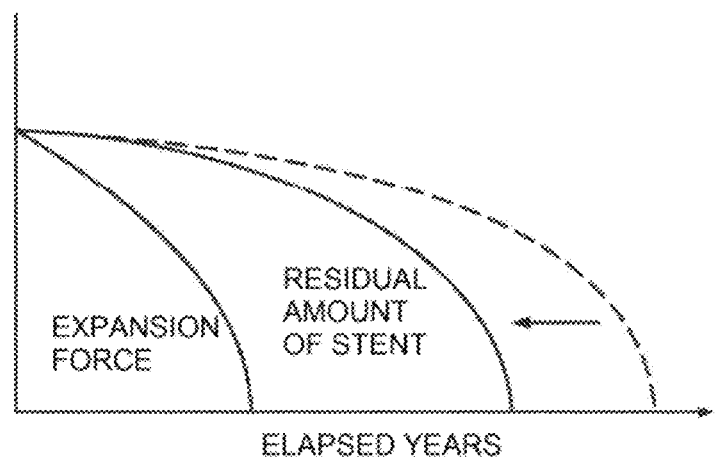
FIG. 6 is a graph for illustrating an effect due to reduction in volume of a link portion.

As described above, since the link portion 120 of the stent 100 according to the exemplary embodiment has the first curved portion 121 and the second curved portion 123, it is possible to reduce the volume (except connection extension portion 130) of the link portion 120 compared with the stent (see dotted line in FIG. 4) having a rectangular cross section. In this way, by reducing the volume of the link portion 120, the following two effects are provided. Note that, in the following description of the effects, an increase in the volume by the connection extension portion 130 is not considered. In addition, FIG. 6 is a view for illustrating an effect due to reduction in the volume of the link portion 120. A horizontal axis indicates the number of elapsed years after indwelling the stent 100 in the blood vessel, and a vertical axis indicates an expansion force with respect to the blood vessel wall W and the residual amount of the stent 100. In addition, in the graph indicating the residual amount of the stent in FIG. 6, a solid line indicates a graph of the residual amount of the stent according to the exemplary embodiment, and a dotted line indicates a graph of the residual amount of the stent having a rectangular cross section according to a comparative example.

Firstly, since the biodegradable material that configures the link portion 120 reduces as the volume of the link portion 120 reduces, an inflammatory response when being indwelled in the blood is reduced.

Secondly, as shown in FIG. 6, since it is possible to eliminate the stent 100 at an early stage (see arrow in FIG. 6) after the expansion force with respect to the blood vessel wall W becomes 0, it is possible to reduce a load on a living body.

As shown in FIG. 4, the connection extension portion 130 has, in the cross section along the connection direction X1, a first gradually decreasing portion 131 that is linked while gradually decreasing from the first curved portion 121 of the link portion 120 toward an edge 130*a* on the upstream side of the blood flow F1, and a second gradually decreasing portion 132 that is linked while gradually decreasing from the second curved portion 123 of the link portion 120 toward an edge 130*b* on a downstream side of the blood flow F1.

The first gradually decreasing portion 131 curves to protrude outward (lower side of FIG. 4) in the radial direction R. In addition, when the stent 100 is indwelled in the blood vessel, it is preferable that the first gradually decreasing portion 131 is provided smoothly and continuous with respect to the blood vessel wall W.

The second gradually decreasing portion 132 curves to protrude outward (lower side of FIG. 4) in the radial direction R. In addition, when the stent 100 is indwelled in the blood vessel, it is preferable that the second gradually decreasing portion 132 is provided smoothly and continuous with respect to the blood vessel wall W.

Note that, it is preferable that a ratio of a length L1, along the connection direction X1 including the first gradually decreasing portion 131 and the first curved portion 121 combined, with respect to a length H along the radial direction R is ⅖ or more.

In addition, it is preferable that a ratio of a length L2, along the connection direction X1 including the second gradually decreasing portion 132 and the second curved portion 123 combined, with respect to the length H along the radial direction R is ⅖ or more.

From the above, the stream or stream-lined shape is formed along the connection direction X1 using the first gradually decreasing portion 131, the first curved portion 121, the linear portion 122, the second curved portion 123, and the second gradually decreasing portion 132. Note that, it is preferable that each above-described portion is provided smoothly and continuous at an interlocking point of each other from the viewpoint of suppressing separation of the blood flow.

According to the stent 100 having such a configuration, the stream shape is provided inward in the radial direction R of the stent 100 along the connection direction X1 by the link portion 120 and the connection extension portion 130, and the blood flow F1 flows along the link portion 120 and the connection extension portion 130. Accordingly, since the blood flow F1 flows along the stream shape provided in a range longer than the connection direction X1 compared with the stent in which the connection extension portion 130 is not provided, the blood flows well.

Furthermore, since the connection extension portion 130 has the first gradually decreasing portion 131 and the second gradually decreasing portion 132, it has a shape in which the blood vessel wall W is easier to cover the stent 100 compared with the stent (see dotted line in FIG. 4) provided with a rectangular cross section according to the comparative example. Therefore, it is possible to perform endothelialization on the stent 100 at an early stage.

Next, a cross-sectional shape along the orthogonal direction X2 of the link portion 120 and the orthogonal extension portion 140 will be described with reference to FIG. 5. Note that, in FIG. 5, a state where the link portion 120 and the orthogonal extension portion 140 are compressed to the blood vessel wall W is shown. In addition, in FIG. 5, an upper side of the drawing is a blood flow side, and a lower side thereof is the blood vessel wall W side. The blood flow F2 along the orthogonal direction X2 in the blood flow F flows along the stream shape of the cross section along the orthogonal direction X2 of the link portion 120 and the orthogonal extension portion 140.

As shown in FIG. 5, the link portion 120 has, in the cross section along the orthogonal direction X2, a third curved portion 124, a linear portion 125, and a fourth curved portion 126 provided in order from the upstream side (left side of FIG. 5) of the blood flow F2.

The third curved portion 124 curves to protrude inward (upper side of FIG. 5) in the radial direction R.

The linear portion 125 is provided smoothly and continuous to the third curved portion 124 in an end portion 124*a* on a downstream side of the third curved portion 124.

The fourth curved portion 126 curves to protrude inward (upper side of FIG. 5) in the radial direction R. In addition, the fourth curved portion 126 is configured such that a tangent line in an end portion 126*a* on an upstream side of the fourth curved portion 126 extends along the linear portion 125. The fourth curved portion 126 is configured to have a curvature smaller than the third curved portion 124.

The fourth curved portion 126 is provided smoothly and continuous to the linear portion 125 in the end portion 126*a* on the upstream side of the fourth curved portion 126.

As described above, since the link portion 120 of the stent 100 according to the exemplary embodiment has the third curved portion 124 and the fourth curved portion 126, it is possible to reduce the volume (except orthogonal extension portion 140) of the link portion 120 compared with the stent (see dotted line in FIG. 5) having a rectangular cross section. In this way, by reducing the volume of the link portion 120, the two effects described above are provided. Note that, in the effects, an increase in the volume by the orthogonal extension portion 140 is not considered.

As shown in FIG. 5, the orthogonal extension portion 140 has, in the cross section along the orthogonal direction X2, a third gradually decreasing portion 141 that is linked while gradually decreasing from the third curved portion 124 of the link portion 120 toward an edge 140a on the upstream side of the blood flow F2, and a fourth gradually decreasing portion 142 that is linked while gradually decreasing from the fourth curved portion 126 of the link portion 120 toward an edge 140b on the downstream side of the blood flow F2.

The third gradually decreasing portion 141 curves to protrude outward (lower side of FIG. 5) in the radial direction R. In addition, when the stent 100 is indwelled in the blood vessel, it is preferable that the third gradually decreasing portion 141 is provided smoothly and continuous with respect to the blood vessel wall W.

The fourth gradually decreasing portion 142 curves to protrude outward (lower side of FIG. 5) in the radial direction R. In addition, when the stent 100 is indwelled in the blood vessel, it is preferable that the fourth gradually decreasing portion 142 is provided smoothly and continuous with respect to the blood vessel wall W.

Note that, it is preferable that a ratio of a length L3 along the orthogonal direction X2, including the third gradually decreasing portion 141 and the third curved portion 124 combined, with respect to the length H along the radial direction R is ⅖ or more.

In addition, it is preferable that a ratio of a length L4 along the orthogonal direction X2, including the fourth gradually decreasing portion 142 and the fourth curved portion 126 combined, with respect to the length H along the radial direction R is ⅖ or more.

From the above, the stream or stream-lined shape is formed along the orthogonal direction X2 using the third gradually decreasing portion 141, the third curved portion 124, the linear portion 125, the fourth curved portion 126, and the fourth gradually decreasing portion 142. Note that, it is preferable that each above-described portion is provided smoothly and continuous at an interlocking point of each other from the viewpoint of suppressing the separation of the blood flow.

According to the stent 100 having such a configuration, the stream shape is provided inward in the radial direction R of the stent 100 along the orthogonal direction X2 using the link portion 120 and the orthogonal extension portion 140, and the blood flow F2 flows along the link portion 120 and the orthogonal extension portion 140. Accordingly, since the blood flow F2 flows along the stream shape provided in a range longer than the orthogonal direction X2 compared with the stent in which the orthogonal extension portion 140 is not provided, the blood flows well.

Furthermore, since the orthogonal extension portion 140 has the third gradually decreasing portion 141 and the fourth gradually decreasing portion 142, it has a shape in which the blood vessel is easier to cover the stent compared with the stent (see dotted line in FIG. 5) provided with a rectangular cross section according to the comparative example. Therefore, it is possible to perform endothelialization on the stent 100 at an early stage.

Next, the action and the effect of the stent 100 of the exemplary embodiment will be described.

The stent 100 is delivered to a stenosed site or an occlusion site formed in a blood vessel using medical equipment for stent delivery such as a balloon catheter.

The delivered stent 100 expands in accordance with widening of a balloon in a stenosed site or an occlusion site within a blood vessel. Note that, the stent 100 may be a self-expanding type.

The stent 100 is indwelled in an expanded state in the blood vessel. Hereinafter, the blood flow F in a vicinity of the blood vessel wall W will be described. Note that, to facilitate understanding, the blood flow F along the axial direction D will be divided into the blood flow F1 along the connection direction X1, and the blood flow F2 along the orthogonal direction X2, and the description will be given respectively. The blood flow F1 along the connection direction X1 flows along the stream shape of the cross section along the connection direction X1 of the link portion 120 and the connection extension portion 130. In addition, the blood flow F2 along the orthogonal direction X2 flows along the stream shape of the cross section of the link portion 120 and the orthogonal extension portion 140 along the orthogonal direction X2.

Figure 7:
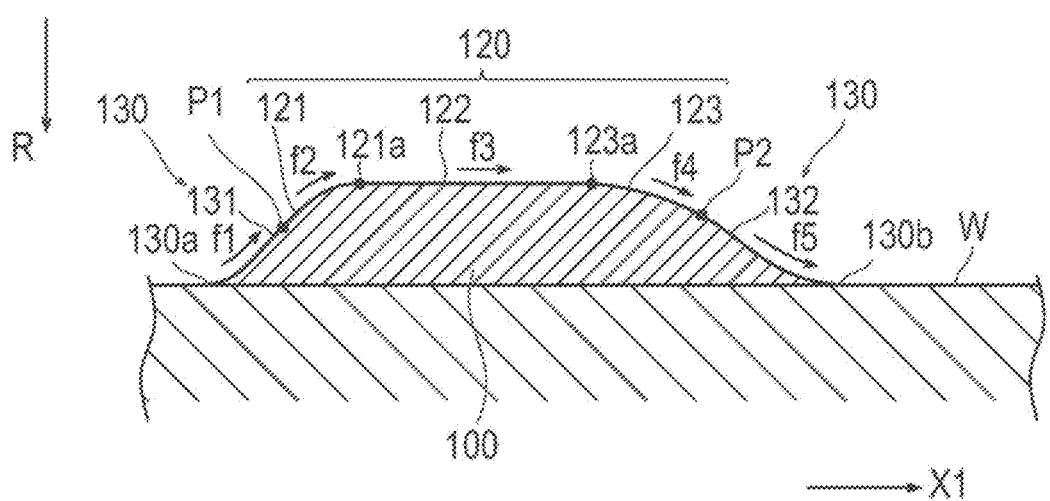
FIG. 7 is a view for illustrating blood movement along a connection direction in a vicinity of the stent.

The blood flow F1 along the connection direction X1 will be described with reference to FIG. 7.

First, the blood flowing to a vicinity of the stent 100 flows along the first gradually decreasing portion 131 (see symbol f1). Here, since the first gradually decreasing portion 131 gradually decreases toward the edge 130a on the upstream side of the blood flow F1, it is possible to suppress occurrence of convection in a vicinity of the edge 130a on the upstream side, and it is possible to suppress the formation of a thrombus.

Next, blood flows through an interlocking point P1 that interlocks the first gradually decreasing portion 131 and the first curved portion 121. Here, since the first gradually decreasing portion 131 and the first curved portion 121 are smoothly continuous at the interlocking point P1, it is possible to suppress the separation of the blood flow at the interlocking point P1. Accordingly, it is possible to suppress the formation of a thrombus at the interlocking point P1.

Next, the blood flows along the first curved portion 121, and flows to the end portion 121a on the downstream side of the first curved portion 121 (see symbol f2). Here, since the first curved portion 121 curves and extends to protrude inward in the radial direction R, the blood flows toward the end portion 121a of the first curved portion 121 so as to gradually approach a direction of the blood flow F1. Therefore, the separation of the blood flow in the end portion 121a reduces, and blood flow in a direction intersecting the direction of the blood flow F1 is suppressed. Therefore, it is possible to suppress the formation of a thrombus in a vicinity of the end portion 121a.

Next, the blood flows along the linear portion 122 (see symbol f3). Here, since the linear portion 122 is provided so as to be parallel to the direction of the blood flow F1, even blood slightly separated from the end portion 121a gradually flows along the direction of the blood flow F1 in the linear portion 122. Therefore, it is possible to suppress the occurrence of convection in a vicinity of the linear portion 122 and it is possible to suppress the formation of a thrombus.

Next, the blood flows through the end portion 123a on the upstream side of the second curved portion 123. Here, since the linear portion 122 and the second curved portion 123 are smoothly continuous at the end portion 123a of the second curved portion 123, it is possible to suppress the separation of the blood flow in a vicinity of the end portion 123a.

Therefore, it is possible to suppress the formation of a thrombus in the vicinity of the end portion 123a.

Next, the blood flows along the second curved portion 123 (see symbol f4). Here, since the second curved portion 123 extends to protrude inward in the radial direction R, the blood flow F1 flows more easily along the second curved portion 123. Therefore, it is possible to suppress the separation of the blood flow F1 from the second curved portion 123, and it is possible to suppress the formation of a thrombus in a vicinity of the second curved portion 123.

Next, the blood flows through an interlocking point P2 of the second curved portion 123 and the second gradually decreasing portion 132. Here, since the second curved portion 123 and the second gradually decreasing portion 132 are smoothly continuous at the interlocking point P2, it is possible to suppress the separation of the blood flow at the interlocking point P2. Accordingly, it is possible to suppress the formation of a thrombus at the interlocking point P2.

Next, the blood flows along the second gradually decreasing portion 132 (see symbol f5). Here, since the second gradually decreasing portion 132 gradually decreases toward the edge 130b on the downstream side of the blood flow F1, it is possible to suppress separation of the blood in a vicinity of the edge 130b on the downstream side.

Figure 8:
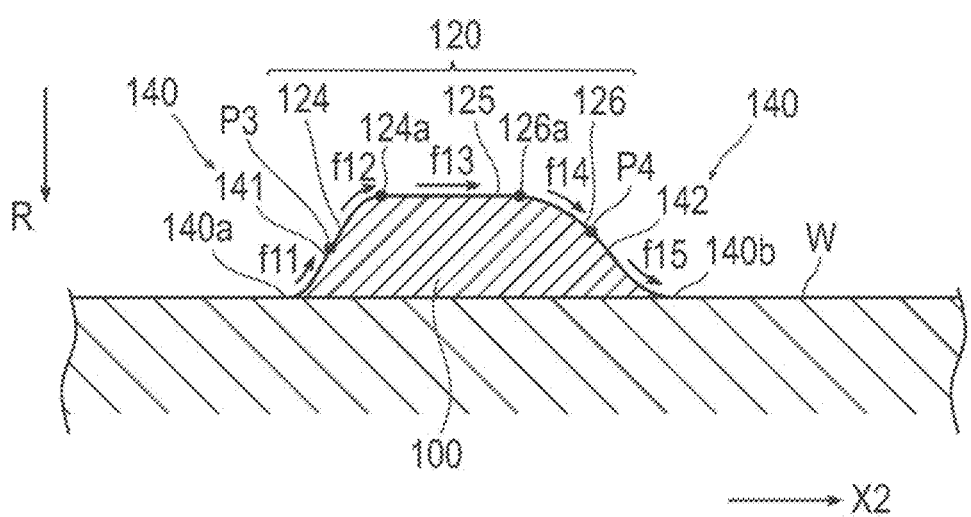
FIG. 8 is a view for illustrating blood movement along an orthogonal direction in the vicinity of the stent.

As described above, the blood flow F1 along the connection direction X1 in the blood flow F has been described. Next, the blood flow F2 along the orthogonal direction X2 will be described with reference to FIG. 8.

First, the blood flowing to the vicinity of the stent 100 flows along the third gradually decreasing portion 141 (see symbol f11). Here, since the third gradually decreasing portion 141 gradually decreases toward the edge 140a on the upstream side of the blood flow F2, it is possible to suppress the occurrence of convection in a vicinity of the edge 140a on the upstream side, and it is possible to suppress the formation of a thrombus.

Next, the blood flows through an interlocking point P3 that interlocks the third gradually decreasing portion 141 and the third curved portion 124. Here, since the third gradually decreasing portion 141 and the third curved portion 124 are smoothly continuous at the interlocking point P3, it is possible to suppress the separation of the blood flow at the interlocking point P3. Accordingly, it is possible to suppress the formation of a thrombus at the interlocking point P3.

Then, the blood flows along the third curved portion 124 and flows to the end portion 124a on the downstream side of the third curved portion 124 (see symbol f12). Here, since the third curved portion 124 curves and extends to protrude inward in the radial direction R, the blood flows toward the end portion 124a of the third curved portion 124 so as to gradually approach a direction of the blood flow F2. Therefore, the separation of the blood flow in the end portion 124a reduces, and blood flow in a direction intersecting the direction of the blood flow F2 is suppressed. Therefore, it is possible to suppress the formation of a thrombus in a vicinity of the end portion 124a.

Next, the blood flows along the linear portion 125 (see symbol f13). Here, since the linear portion 125 is provided so as to be parallel to the direction of the blood flow F2, even blood slightly separated from the end portion 124a gradually flows along the direction of the blood flow F2 in the linear portion 125. Therefore, it is possible to suppress the occurrence of convection in a vicinity of the linear portion 125 and it is possible to suppress the formation of a thrombus.

Next, the blood flows through the end portion 126a on a distal side of the fourth curved portion 126. Here, since the linear portion 125 and the fourth curved portion 126 are smoothly continuous at the end portion 126a of the fourth curved portion 126, it is possible to suppress the separation of the blood flow in a vicinity of the end portion 126a. Therefore, it is possible to suppress the formation of a thrombus in the vicinity of the end portion 126a.

Next, the blood flows along the fourth curved portion 126 (see symbol f14). Here, since the fourth curved portion 126 extends to protrude inward in the radial direction R, the blood flow F2 flows more easily along the fourth curved portion 126. Therefore, it is possible to suppress the separation of the blood flow F2 from the fourth curved portion 126, and it is possible to suppress the formation of a thrombus in a vicinity of the fourth curved portion 126.

Next, the blood flows through an interlocking point P4 of the fourth curved portion 126 and the fourth gradually decreasing portion 142. Here, since the fourth curved portion 126 and the fourth gradually decreasing portion 142 are smoothly continuous at the interlocking point P4, it is possible to suppress the separation of the blood flow at the interlocking point P4. Accordingly, it is possible to suppress the formation of a thrombus at the interlocking point P4.

Next, the blood flows along the fourth gradually decreasing portion 142 (see symbol f15). Here, since the fourth gradually decreasing portion 142 gradually decreases toward the edge 140b on the downstream side of the blood flow F2, it is possible to suppress the separation of the blood in a vicinity of the edge 140b on the downstream side.

As described above, the blood flow F2 along the orthogonal direction X2 in the blood flow F has been described.

As described above, the stent 100 of the exemplary embodiment includes the linear struts 110 that form an outer periphery of a cylindrical shape in which a gap g is formed, the link portion 120 that connects the struts 110 to each other in the gap g, and the connection extension portion 130 that extends along the connection direction X1 of the link portion 120. The link portion 120 has, in the cross section along the connection direction X1, the first curved portion 121 that is provided on the upstream side in the connection direction X1, and curves to protrude inward in the radial direction R, and the second curved portion 123 that is provided on the downstream side of the connection direction X1, and curves to protrude inward in the radial direction R. The connection extension portion 130 has, in the cross section along the connection direction X1, the first gradually decreasing portion 131 that is linked while gradually decreasing from the first curved portion 121 toward the edge 130a on the upstream side of the connection direction X1 and the second gradually decreasing portion 132 that is linked while gradually decreasing from the second curved portion 123 toward the edge 130b on the downstream side of the connection direction X1. According to the stent 100 having such a configuration, the stream shape is provided inward in the radial direction R of the stent 100 by the link portion 120 and the connection extension portion 130, and the blood flow F1 along the connection direction X1 in the blood flow F flows along the link portion 120 and the connection extension portion 130. Accordingly, since the blood flow F1 flows along the stream shape provided in a range longer than the connection direction X1, the blood flows well along the connection direction X1. Therefore, it is possible to suppress the formation of a thrombus in a vicinity of the link portion 120.

In addition, the stent 100 further has the orthogonal extension portion 140 that extends along the orthogonal direction X2. The link portion 120 has, in the cross section along the orthogonal direction X2, the third curved portion 124 that is provided on the upstream side in the orthogonal direction X2 and curves to protrude inward in the radial direction R, and the fourth curved portion 126 that is provided on the downstream side in the orthogonal direction X2 and curves inward in the radial direction R. The orthogonal extension portion 140 has, in the cross section along the orthogonal direction X2, the third gradually decreasing portion 141 that is linked while gradually decreasing from the third curved portion 124 toward the edge 140a on the upstream side in the orthogonal direction X2, and the fourth gradually decreasing portion 142 that is linked while gradually decreasing from the fourth curved portion 126 toward the edge 140b on the downstream side in the orthogonal direction X2. According to the stent 100 having such a configuration, the stream shape is provided inward in the radial direction R of the stent 100 using the link portion 120 and the orthogonal extension portion 140, and the blood flow F2 along the orthogonal direction X2 in the blood flow F flows along the link portion 120 and the orthogonal extension portion 140. Accordingly, since the blood flow F2 flows along the stream shape provided in a range longer than the orthogonal direction X2, the blood flows well along the orthogonal direction X2. Therefore, it is possible to more suitably suppress the formation of a thrombus in the vicinity of the link portion 120.

In addition, the first curved portion 121 is provided on the proximal side, which is the hand operation side, the second curved portion 123 is provided on the distal side that is to be inserted in the vivo, and the second curved portion 123 has a curvature smaller than the first curved portion 121. According to the stent 100 having such a configuration, the blood flow F1 flows more easily along the second curved portion 123. Therefore, it is possible to suppress the separation of the blood flow F1 from the second curved portion 123, and it is possible to suppress the formation of a thrombus in the vicinity of the second curved portion 123.

In addition, the link portion 120 further has, in the cross section along the connection direction X1, the linear portion 122 that interlocks the first curved portion 121 and the second curved portion 123. For this reason, even the blood slightly separated from the end portion 121a of the first curved portion 121 gradually flows along the direction of the blood flow F1 in the linear portion 122. Therefore, it is possible to suppress the occurrence of convection in the vicinity of the linear portion 122, and it is possible to suppress the formation of a thrombus in the vicinity of the linear portion 122.

In addition, the connection extension portion 130 has the concave portion 130c that is arcuately recessed toward the link portion 120. According to the configuration, since the connection extension portion 130 is formed in a paddle shape, the blood flow is improved, and it is possible to more suitably suppress the formation of a thrombus in the vicinity of the link portion 120.

In addition, the stent 100 is formed of a biodegradable polymer. According to the configuration, since the stent 100 according to the exemplary embodiment can be manufactured by, for example, an injection molding, it is easier to manufacture the stent 100.

The disclosure herein is not limited to the exemplary embodiment and the modification examples described above, and can be variously modified within the scope of the claims.

For example, in the above-described exemplary embodiment, the link portion 120, the connection extension portion 130, and the orthogonal extension portion 140 are integrally configured with the struts 110. However, the link portion 120, the connection extension portion 130, and the orthogonal extension portion 140 may be configured separately from the struts 110. At this time, the link portion 120, the connection extension portion 130, and the orthogonal extension portion 140 are formed of, for example, a biodegradable material. On the other hand, the struts 110, for example, may be formed of a non-biodegradable material. Examples of such a material include stainless steel, a cobalt-based alloy such as a cobalt-chromium alloy (for example, a CoCrWNi alloy), elastic metal such as a platinum-chromium alloy (for example, a PtFeCrNi alloy), and a super-elastic alloy such as a nickel-titanium alloy.

In addition, in the above-described exemplary embodiment, the stent 100 is configured such that the plurality of struts 110 is disposed along the axial direction D1. However, the strut of the stent may be configured in a spiral shape along the axial direction D1.

In addition, in the above-described exemplary embodiment, the connection extension portion 130 has the concave portion 130c that is arcuately recessed toward the link portion 120. However, a connection extension portion may have a configuration in which a concave portion is not provided. In addition, in addition to the connection extension portion 130, the orthogonal extension portion 140 may have a concave portion that is arcuately recessed toward the link portion 120.

In addition, in the above-described exemplary embodiment, the stent 100 includes the orthogonal extension portion 140. However, the stent may not include an orthogonal extension portion. At this time, it is preferable that the link portion 120 of the stent 100 in the expanded state is formed along the axial direction D1.

In addition, in the above-described exemplary embodiment, the second curved portion 123 has a curvature smaller than the first curved portion 121. However, it is not limited thereto, and a second curved portion may be configured to have the same curvature with a first curved portion, or, a curvature larger than the first curved portion.

In addition, in the above-described exemplary embodiment, the link portion 120 has, in the cross section along the connection direction X1, the linear portion 122 that interlocks the first curved portion 121 and the second curved portion 123. However, the link portion may not have a linear portion.

In addition, in the above-described exemplary embodiment, the fourth curved portion 126 is configured have a curvature smaller than the third curved portion 124. However, it is not limited thereto, and a fourth curved portion may be configured to have the same curvature with a third curved portion, or, a curvature larger than the third curved portion.

In addition, in the above-described exemplary embodiment, the link portion 120 has, in the cross section along the orthogonal direction X2, the linear portion 125 that interlocks the third curved portion 124 and the fourth curved portion 126. However, the link portion may not have a linear portion.

The detailed description above describes features, characteristics and operational aspects of embodiments of a stent representing examples of the stent disclosed herein. The disclosure and the present invention are not limited, however, to the precise embodiments and variations described. Various changes, modifications and equivalents could be effected by one skilled in the art without departing from the spirit and scope of the disclosure as defined in the appended claims. It is expressly intended that all such changes, modifications and equivalents which fall within the scope of the claims are embraced by the claims.

What is claimed is:

1. A stent comprising:
   a plurality of linear struts that form an outer periphery of a cylindrical shape in which a gap is formed between adjacent ones of the plurality of struts;
   a link portion that connects the struts to each other in the gap; and
   a connection extension portion that extends along a connection direction of the link portion,
   wherein, in a cross section along the connection direction, the link portion includes,
   a first curved portion that is provided on one end of the connection direction and curves to protrude inward in a radial direction, and
   a second curved portion that is provided on the other end of the connection direction and curves to protrude inward in the radial direction, and
   wherein, in a cross section along the connection direction, the connection extension portion includes,
   a first gradually decreasing portion gradually decreasing from the first curved portion toward an edge on one end of the connection direction, and
   a second gradually decreasing portion gradually decreasing from the second curved portion toward an edge on the other end of the connection direction.

2. The stent according to claim 1, further comprising:
   an orthogonal extension portion that extends along an orthogonal direction that is orthogonal to the connection direction of the link portion,
   wherein, in a cross section along the orthogonal direction, the link portion includes,
   a third curved portion that is provided on one end of the orthogonal direction and curves to protrude inward in the radial direction, and
   a fourth curved portion that is provided on the other end of the orthogonal direction and curves to protrude inward in the radial direction, and
   wherein, in a cross section along the orthogonal direction, the orthogonal extension portion includes,
   a third gradually decreasing portion gradually decreasing from the third curved portion toward an edge on one end of the orthogonal direction, and
   a fourth gradually decreasing portion gradually decreasing from the fourth curved portion toward an edge on the other end of the orthogonal direction.

3. The stent according to claim 1,
   wherein the first curved portion is provided on a proximal side, that is configured to be a hand operation side,
   the second curved portion is provided on a distal side, that is configured to be inserted in vivo, and
   the second curved portion has a curvature smaller than the first curved portion.

4. The stent according to claim 1,
   wherein, in a cross section along the connection direction, the link portion further includes,
   a linear portion that interlocks the first curved portion and the second curved portion.

5. The stent according to claim 1,
   wherein the connection extension portion has a concave portion that is arcuately recessed toward the link portion.

6. The stent according to claim 1, wherein the stent is manufactured by injection molding or laminate molding.

7. The stent according to claim 1, wherein the stent is formed of a biodegradable polymer.

8. The stent according to claim 1, wherein the link portion includes an interlock portion configured to interlock the struts to each other.

9. The stent according to claim 1, wherein the first gradually decreasing portion and the first curved portion define a first length along the connection direction and a first height along the radial direction, a ratio of the first length to the first height being ⅖ or more.

10. The stent according to claim 9, wherein the second gradually decreasing portion and the second curved portion define a second length along the connection direction, a ratio of the second length to the first height being ⅖ or more.

11. A stent comprising:
    a plurality of linear struts that form an outer periphery of a cylindrical shape in which a gap is formed between adjacent ones of the plurality of struts;
    a link portion that connects the struts to each other in the gap; and
    a connection extension portion that extends along a connection direction of the link portion,
    wherein, in a cross section along the connection direction, the link portion includes:
    an inner periphery distal end point and an inner periphery proximal end point on an inner peripheral side of a cylinder,
    an inner peripheral linear portion that interlocks the inner periphery distal end point and the inner periphery proximal end point,
    a first distal end curved portion that smoothly interlocks with the inner periphery distal end point, and
    a first proximal end curved portion that smoothly interlocks with the inner periphery proximal end point,
    wherein, in a cross section along the connection direction, the connection extension portion includes:
    an outer periphery distal end point and an outer periphery proximal end point on an outer peripheral side of a cylinder,
    an outer peripheral linear portion that interlocks the outer periphery distal end point and the outer periphery proximal end point,
    a second distal end curved portion that smoothly interlocks the outer periphery distal end point and the first distal end curved portion, and
    a second proximal end curved portion that smoothly interlocks the outer periphery proximal end point and the first proximal end curved portion.

12. The stent according to claim 11, wherein the first distal end curved portion and the first proximal end curved portion curve to protrude inward in a radial direction.

13. The stent according to claim 11, wherein the second distal end curved portion and the second proximal end curved portion curve to protrude outward in a radial direction.

14. The stent according to claim 11, wherein the second distal end curved portion gradually decreases from the first distal end curved portion of the link portion toward the outer periphery distal end point, and a second proximal end curved portion gradually decreases from the first proximal end curved portion of the link portion toward outer periphery proximal end point.

15. The stent according to claim 11, further comprising:
    an orthogonal extension portion that extends along an orthogonal direction that is orthogonal to the connection direction of the link portion,
    wherein, in a cross section along the orthogonal direction, the link portion includes, a third distal end curved portion that is provided on one end of the orthogonal direction and curves to protrude inward in the radial direction, and a third proximal end curved portion that is provided on the other end of the orthogonal direction and curves to protrude inward in the radial direction, and wherein, in a cross section along the orthogonal direction, the orthogonal extension portion includes, a fourth distal end curved portion gradually decreasing from the third distal end curved portion toward an edge on one end of the orthogonal direction, and a fourth proximal end curved portion gradually decreasing from the third proximal end curved portion toward an edge on the other end of the orthogonal direction.

16. The stent according to claim 11, wherein the first distal end curved portion and the second distal end curved portion define a first length along the connection direction and a first height along the radial direction, a ratio of the first length to the first height being ⅖ or more.

17. The stent according to claim 16, wherein the first proximal end curved portion and the second proximal end curved portion define a second length along the connection direction, a ratio of the second length to the first height being ⅖ or more.

18. The stent according to claim 11, wherein the connection extension portion has a concave portion that is arcuately recessed toward the link portion.

* * * * *